United States Patent

Bohlmann

[11] Patent Number: 5,786,474
[45] Date of Patent: Jul. 28, 1998

[54] N-FLUOROSULFONIMIDES, PROCESS FOR THEIR PRODUCTION, AS WELL AS THEIR USE AS FLUORINATING AGENTS

[75] Inventor: Rolf Bohlmann, Berlin, Germany

[73] Assignee: Schering Aktiengesellschaft, Berlin, Germany

[21] Appl. No.: 537,769

[22] PCT Filed: Apr. 20, 1994

[86] PCT No.: PCT/EP94/01251

§ 371 Date: Feb. 1, 1996

§ 102(e) Date: Feb. 1, 1996

[87] PCT Pub. No.: WO94/24098

PCT Pub. Date: Oct. 27, 1994

[30] Foreign Application Priority Data

Apr. 20, 1993 [DE] Germany ............ 43 13 664.8

[51] Int. Cl.$^6$ ............ C07D 285/16; C07D 285/00; C07D 205/00; C07C 303/00

[52] U.S. Cl. ............ 544/5; 548/123; 548/950; 564/82

[58] Field of Search ............ 544/5; 548/950, 548/123; 564/82

[56] References Cited

U.S. PATENT DOCUMENTS

| | | | |
|---|---|---|---|
| 4,828,764 | 5/1989 | DesMarteau et al. | 260/397.45 |
| 5,072,040 | 12/1991 | Armand | 564/82 |
| 5,254,732 | 10/1993 | Differding et al. | 564/82 |
| 5,403,957 | 4/1995 | Wagner et al. | 564/82 |
| 5,552,533 | 9/1996 | Poss et al. | 536/7.2 |

FOREIGN PATENT DOCUMENTS 0252431  2/1987  European Pat. Off. .

OTHER PUBLICATIONS

Geiseler et. al., "Über Das Schwingungsspektrum . . . ", Chemische Berichte, vol. 91 (1958), pp. 1881–1891.
Aleinikov et al, Fluorine Chemistry, vol. 58, No. 2–3, 1992, p. 141 "Synthesis and . . . N–Fluoroalkylsulfonamides."
Barnette, J. of ACS, vol. 106, No. 2, 1984, pp. 452–454 "N–Fluoro–N–Alkylsulfonamides . . . Carbanions."
Davis et al, Tetrahedron Letters, vol. 132, No. 13, 1991, pp. 1631–1634 "N–Fluoro–o . . . Fluorinating Reagent."
Differding, Synlett, No. 03, 1991, pp. 187–189 "N–Fluorobenzenesulfonimides . . . Fluorinations."

*Primary Examiner*—Mukund J. Shah
*Assistant Examiner*—Tamthom T. Ngo
*Attorney, Agent, or Firm*—Millen, White, Zelano, & Branigan, P.C.

[57] ABSTRACT

N-fluorosulfonimides of general formula I $$(R^1-SO_2)_2NF \qquad (I),$$

in which $R^1$ means a methyl group each or together a group $-(CH_2)_n-$ with n=1, 2 or 3, especially N-flouromethanesulfonimide, $(CH_3SO_2)_2NF$, their production as well as their use for electrophilic fluorination of activated C—H bonds of organic molecules, are described.

15 Claims, No Drawings

N-FLUOROSULFONIMIDES, PROCESS FOR THEIR PRODUCTION, AS WELL AS THEIR USE AS FLUORINATING AGENTS

This is a 371 application of PCT/EP 94/01251 filed on Apr. 20, 1994.

this invention relates to N-fluorosulfonimides, which are suitable as fluorinating reagents.

In the search for new pharmaceutical or agrochemical products, fluorinated substances have great importance. For the production of these compounds, electrophilic fluorinating reagents play a special role since they make it possible to exchange activated hydrogens with fluorine in one step. Known reagents of this type are, i.e., the gas perchloryl fluoride, which tends toward reactions that are too explosive, cesium peroxofluorosulfate, which is very difficult to store, the unstable acetyl hypofluorite, the very reactive perfluoromethane-sulfonimide, N-fluorophenyl sulfonimide (E. Differding and H. Ofner, "Synlett," p. 187, 1991), and N-fluoro-ortho-benzodisulfonimide (F. A. Davis and W. Han, "Tetrahedron Letters" 32, p. 1631, 1991).

Although with N-fluorophenyl sulfonimide, a readily manageable, easily accessible reactive agent for electrophilic fluorination is available, its content of 60.2 g of active fluorine/kg of fluorinating agent (formula weight of N-fluorophenyl sulfonimide 315.3 g/mol) is relatively low.

The object of this invention is to provide new compounds for more effective use as fluorinating agents for the electrophilic fluorination of activated C—H bonds.

It has now been found that the new N-fluorosulfonimides of general formula I $(R^1-SO_2)_2NF$ (I), in which $R^1$ means a methyl group each or together a group $-(CH_2)_n-$ with n=1, 2 or 3, can be produced simply and can be used extremely well for electrophilic fluorination of activated C—H bonds.

Within the scope of this invention, N-fluoromethanesulfonimide and N-fluoro[1,3,2]dithiazinane-1,1,3,3-tetraoxide are preferred.

The fluorosulfonimides of general formula I according to the invention exhibit a higher active fluorine content because of their considerably lower formula weight as compared with N-fluorophenylsulfonimide; for example, the N-fluoromethane-sulfonimide according to the invention with a formula weight of 191.2 g/mol has an active fluorine content of 99.3 g of fluorine/kg.

The compounds of general formula I are readily soluble in many organic solvents. The sulfonimide that remains after fluorination from the active compound has significantly better water solubility than phenylsulfonimide. As a result, the sulfonimide that is formed in each case can be separated quite simply by washing the organic phase, for example, diethyl ether, in which the fluorinated product is present. Expensive chromatographic purification steps and the use of large amounts of solvent are thus avoided.

It is considered surprising that the compounds of general formula I according to the invention, such as the known N-fluorophenylsulfonimide, are stable. In the case of the compounds of general formula I, it would actually have been expected that the very reactive fluorine would be transferred intramolecularly and/or intermolecularly to radical $R^1$ and that the compounds of general formula I would fluorinate themselves, as it were.

The production of the N-fluorosulfonimides of general formula I is done according to the invention by reacting the easily accessible sulfonimides of general formula II $(R^1SO_2)_2NH$ (II), in which $R^1$ means a methyl group each or together a group $-(CH_2)_n-$ with n=1, 2 or 3, with elementary fluorine in a suitable organic solvent.

Acetonitrile is preferably used as solvent. The reaction temperature is between 0° C. and –50° C.; it is preferably –40° C. fluorination is preferably done in the presence of an alkali fluoride, such as, for example, sodium fluoride, and if necessary, the product can be purified chromatographically ($SiO_2$eluent, e.g., $CH_2CL_2$).

Advantageously, the N-fluorosulfonimides according to the invention can be used for fluorination of activated C—H bonds in aromatic compounds, enol ethers, enolates or arylates. In this case, the procedure according to the invention is normally such that the corresponding C—H bond is first deprotonated by reacting the substrate with a strong base, such as, for example, sodium hydride, lithium diisopropylamide, or an alkyllithium compound, such as, for example, tert-butyllithium, and the thus activated C—H bond is then fluorinated by allowing it to react with an N-fluorosulfonimide of general formula I. Depending on the base thickness and the reactivity of the C—H bond, the deprotonation is performed at a temperature of between –20° C. up to +40° C., and the actual fluorination is performed at a temperature of between –100° C. and +20° C.

After working-up, the fluorinated compounds accumulate in very high yields of up to 98%.

This invention is explained in more detail based on the examples below. The sample applications are to demonstrate the universal suitability of the compounds of general formula I for electrophilic fluorination of C—H activated compounds.

EXAMPLE 1

N-Fluoromethanesulfonimide 60 liters of a mixture of 10 parts by volume of fluorine and 90 parts by volume of nitrogen is introduced into a solution of 15 g of dimethyl sulfonimide (helferich and Flechsig, "Berichte [Reports])" 75, p. 532, 1942) in 200 ml of acetonitrile at –40° C. in the presence of 14.5 g of sodium fluoride powder within 2.5 hours. Then, it is flushed with pure nitrogen, concentrated by evaporation in a vacuum, taken up with 200 ml of ethyl acetate, filtered on Celite, concentrated by evaporation in a vacuum, and recrystallized from ethyl acetate/hexane. 14.9 g of N-fluoromethanesulfonimide is obtained as pale yellow crystals with a melting point of 45°–48° C. If necessary, it can be purified chromatographically on silica gel with dichloromethane.

EXAMPLE 2

N-Fluoro[1,3,2]dithiazinane-1,1,3,3-tetraoxide 0.5 l of a mixture of 10 parts by volume of fluorine and 90 parts by volume of nitrogen is introduced into a solution of 370 mg of [1,3,2]dithiazinane-1,1,3,3-tetraoxide (Geisler and Kuschmiers, "Chem. Ber." 91, p. 1881, 1958) in 23 ml of acetonitrile at –40° C. in the presence of 82 mg of sodium fluoride powder within 9 minutes. Then, it is flushed with pure nitrogen, concentrated by evaporation in a vacuum, taken up with dichloromethane, chromatographed on 60 g of silica gel, concentrated by evaporation in a vacuum, and recrystallized from acetone/hexane. 331 mg of N-fluoromethanesulfonimide is obtained as crystals with a melting point of 171°–172° C.

SAMPLE APPLICATIONS

2-Fluoro-2-phenyl-malonic acid diethyl ester

A solution of 1.18 g of 2-phenyl-malonic acid diethyl ester in 10 ml of dimethylformamide is stirred with 200 mg of sodium hydride (60% in oil) for 1 hour at 20° C., mixed slowly with 956 mg of N-fluoromethanesulfonimide at 0° C., and stirred for 30 minutes. Then, it is diluted with water, extracted with diethyl ether, washed with water, dried on sodium sulfate, and concentrated by evaporation in a vacuum. 1.353 g of crude 2-fluoro-2-phenyl-malonic acid diethyl ester is obtained.

2-Fluoro-1-phenyl-propan-1-one

A solution of 268 mg of 1-phenyl-propan-1-one in 1.5 ml of tetrahydrofuran is added at 0° C. to 1.3 ml of a 1.6 molar solution of lithium diisopropylamide in tetrahydrofuran, stirred for 15 minutes, cooled to −78° C., mixed with 382 mg of N-fluoromethanesulfonimide in 4 ml of tetrahydrofuran, and heated slowly to room temperature. Then, it is diluted with water, extracted with diethyl ether, washed with water, dried on sodium sulfate, and concentrated by evaporation in a vacuum. 358 mg of crude 2-fluoro-1-phenyl-propan-1-one is obtained.

9-Fluoroanthracene

A solution of 514 mg of 9-bromoanthracene in 5 ml of tetrahydrofuran/diethyl ether (1:1) is mixed at −78° C. with 1.5 ml of a 1.4 molar tert-butyllithium-in-pentane solution, stirred for 30 minutes at −78° C., mixed with 382 of N-fluoromethanesulfonimide, stirred for 1 hour at −78° C., and heated slowly to room temperature. Then, it is diluted with water, extracted with ethyl acetate, washed with water, dried on sodium sulfate, and concentrated by evaporation in a vacuum. 606 mg of crude 9-fluoroanthracen is obtained.

I claim:

1. An N-fluorosulfonimide of formula I $$(R^1\text{—}SO_2)_2NF \qquad (I),$$

in which

R$^1$ means a methyl group each or together a group of —(CH$_2$)$_n$— with n=1, 2 or 3.

2. A compound of claim 1, wherein said compound is N-fluoromethanesulfonimide, (CH$_3$SO$_2$)$_2$NF.

3. A compound of claim 1, wherein said compound is N-fluoro-[1,3,2]dithiazinane-1,1,3,3-tetraoxide,

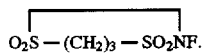

4. A method for electrophilic fluorination of activated C—H bonds of organic molecules which comprises fluorinating an activated C—H on an organic molecule with a fluorinating agent which is an N-fluorosulfonimide of formula I of claim 1.

5. The N-fluorosulfonimide of claim 1, wherein R$^1$ are together a group —(CH$_2$)$_n$— where n=1, 2 or 3.

6. The method of claim 4, wherein, before fluorinating, the organic molecule with C—H bond is deprotonated by reaction with a strong base to activate the C—H bond.

7. The method of claim 4, wherein the fluorinating is conducted at a temperature of between −100° C. and +20° C.

8. The method of claim 6, wherein the deprotonation is conducted at a temperature of between −20° C. and +40° C. and the fluorinating at a temperature between −100° C. and +20° C.

9. A process for the production of an N-fluorosulfonimide of formula I $$(R^1\text{—}SO_2)_2NF \qquad (I),$$

in which

R$^1$ means a methyl group each or together a group —(CH$_2$)$_n$— with n=1, 2 or 3, which comprises fluorinating a sulfonimide of formula II $$(R^1\text{—}SO_2)_2NF \qquad (II),$$

in which

R$^1$ means a methyl group each or together a group —(CH$_2$)$_n$— with n=1, 2 or 3, with elementary fluorine.

10. The process according to claim 9, wherein the sulfonimide of formula II is fluorinated in acetonitrile as a solvent.

11. The process according to claim 9, wherein the sulfonimide of formula II is fluorinated at a temperature of between 0° C. and −50° C.

12. The method of claim 9, wherein the fluorinating is conducted in the presence of an alkali fluoride.

13. A process according to claim 10, wherein it is fluorinated as a temperature of between 0° C. and −50° C.

14. The process of claim 11, wherein the temperature is −40° C.

15. The process of claim 3, wherein the temperature is −40° C.

* * * * *